United States Patent [19]

Bartoszek-Loza

[11] Patent Number: 4,515,667
[45] Date of Patent: May 7, 1985

[54] NOVEL CATALYSTS AND PROCESSES FOR THE PHOTOCHEMICAL DECARBOXYLATION OF ALPHA-HYDROXY CARBOXYLIC ACIDS

[75] Inventor: Rosemary Bartoszek-Loza, Solon, Ohio

[73] Assignee: The Standard Oil Company, Cleveland, Ohio

[21] Appl. No.: 515,233

[22] Filed: Jul. 19, 1983

[51] Int. Cl.$^3$ .............................................. C07C 3/24
[52] U.S. Cl. .................................................. 204/162 R
[58] Field of Search ................................... 204/162 R

[56] References Cited

U.S. PATENT DOCUMENTS

| 4,264,421 | 4/1981 | Bard et al. | 204/157.10 R |
|---|---|---|---|
| 4,275,247 | 6/1981 | Harris | 568/767 |
| 4,303,486 | 12/1981 | Bard et al. | 204/162 R |
| 4,371,431 | 2/1983 | Switzer et al. | 204/59 R |

OTHER PUBLICATIONS

Izumi, I. et al., NTIS No. AD-A 089068, Gov. Rep. Announce, Index, (1981), vol. 81(1), p. 65.
Izumi, I. et al., NTIS No. AD-A091973, Gov. Rep. Announce, Index (1981), vol. 81(7) p. 1339.
Bard, A. J., Science, vol. 207, pp. 139–144 (1980).
Euler, H. et al., Biochemische Zeitschrift, vol. 51, pp. 97–106 (1913).
Baudisch, O., Biochemische Zeitschrift, vol. 103, pp. 59–62 (1920).
Muller, R., Biochemische Zeitschrift, vol. 178, pp. 77–78 (1926).
Burns, G. R., Journal of the American Chemical Society, vol. 51, pp. 3165–3171 (1929).

Primary Examiner—Ben R. Padgett
Assistant Examiner—M. Markowitz
Attorney, Agent, or Firm—Thomas P. Schur; Joseph G. Curatolo; Larry W. Evans

[57] ABSTRACT

Alpha-hydroxy carboxylic acids, such as lactic acid and mandelic acid, are photochemically converted to form high yields of the corresponding alcohol by irradiating a solution containing the alpha-hydroxy carboxylic acid in contact with the semiconductor catalyst material. The semiconductor catalyst material is preferably a metal titanium oxide. The photochemical reaction may be carried out over a wide range of temperatures and pressures and in an oxidative or inert atmosphere.

13 Claims, No Drawings

NOVEL CATALYSTS AND PROCESSES FOR THE PHOTOCHEMICAL DECARBOXYLATION OF ALPHA-HYDROXY CARBOXYLIC ACIDS

BACKGROUND OF THE INVENTION

The present invention relates to catalysts and processes for the photochemical decarboxylation of alpha-hydroxy carboxylic acids to selectively form the corresponding alcohols.

The realization that petroleum feedstocks are limited, nonrenewable resources has stirred interest in the production of what are considered petroleum-derived products by alternative technological means, such as the conversion of biomass to useful hydrocarbons.

As an example, there are now three commercial processes for the production of ethanol: synthesis from ethylene or formation as a by-product of n-butane oxidation, both of which are reliant on petroleum feedstocks, and fermentation of sugar-containing carbohydrates which is a time-consuming process. Currently, most U.S. production of ethanol is derived from ethylene, while internationally fermentation accounts for more than half of the ethanol production. Alternative technological means are being considered for producing alcohols such as ethanol. Alcohols may be obtainable from biomass-derived compounds such as alpha-hydroxy carboxylic acids. Such a process may utilize a photochemical reaction.

It is well known that chemical compounds may be converted into other useful chemicals by means of photo-induced reactions. Euler and Ryd reported in *The Decomposition of Lactic Acid and Tannic Acid in Ultraviolet Light,* Biochemische Zeitschrift, Vol. 51, pp. 97–103, 1913, that lactic acid undergoes cleavage at 70° C. in the presence of ultraviolet light to form formic acid and acetaldehyde and that these products were rapidly converted to ethanol and carbon dioxide. No yields of ethanol were reported.

Photochemical processes generally utilize a catalyst in conjunction with light to obtain the desired reaction. Recently, semiconductor materials have been utilized as catalysts for selective photo-induced chemical reactions. One such semiconductor material is titanium dioxide. U.S. Pat. No. 4,303,486 to Bard et al. discloses heterogeneous photocatalytic decarboxylation of saturated carboxylic acids to form carbon dioxide and the corresponding alkanes. Bard et al. utilized titanium dioxide as the catalyst for this photo-induced reaction. The catalyst was anatase and could be doped and/or platinized. Bard et al. did not disclose product yields.

While photo-induced chemical reactions and semiconductor materials are known, the application of semiconductor materials to photo-induced chemical reactions is not well known nor is it predictable. Catalytic activity of one reaction system does not imply that similar conditions and catalysts will behave in a similar manner when applied to a different reaction.

It would be a significant advance in the field of photochemistry to provide means for producing what are considered petroleum-derived products from materials that are not petroleum-based. Specifically, it would be a technical contribution to the area of photo-induced chemical reactions to provide means for the production of alcohols from alpha-hydroxy carboxylic acids.

Thus, it is an object of this invention to provide novel catalysts for the photo-induced decarboxylation of alpha-hydroxy carboxylic acids to predominantly form the corresponding alcohols.

It is another object of this invention to provide a photochemical process for the decarboxylation of alpha-hydroxy carboxylic acids.

These and other objects of the invention will become apparent in the description of the invention and examples which follow.

SUMMARY OF THE INVENTION

The present invention relates to a process for the photochemical decarboxylation of an alpha-hydroxy carboxylic acid to the corresponding alcohol which process comprises irradiating a mixture of (a) a solution of an alpha-hydroxy carboxylic acid and (b) a semiconductor catalyst material.

DETAILED DESCRIPTION OF THE INVENTION

In accordance with this invention, there is provided a catalyst comprising a semiconductor material and a process whereby the catalyst selectively converts alpha-hydroxy carboxylic acids to corresponding alcohols and carbon dioxide.

Alpha-hydroxy carboxylic acids may be represented by the formula

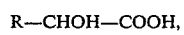

R—CHOH—COOH, wherein R may be hydrogen or an alkyl, alkenyl, aryl, alkaryl, cycloalkyl or cycloalkenyl radical having from 1 to about 20 carbon atoms, and preferably having from 1 to about 12 carbon atoms.

Typical alpha-hydroxy carboxylic acids include mandelic acid, alpha-hydroxy isobutyric acid, alpha-ethyl-alpha-hydroxybutyric acid, alpha-hydroxy-alpha-methylbutyric acid, alpha-isopropyl-mandelic acid, lactic acid, benzylic acid and phenyllactic acid.

The reaction by which alpha-hydroxy carboxylic acids are converted to alcohols may be represented by formula (I) below.

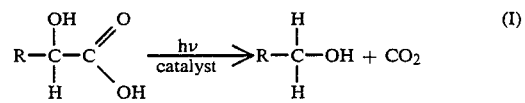

When the alpha-hydroxy carboxylic acid is lactic acid and is photochemically converted in accordance with this invention, the corresponding alcohol that is produced in high yields is ethanol.

Generally, it has been observed that when an alpha-hydroxy carboxylic acid is irradiated in the absence of a semiconductor catalyst material, then from 0 to about 15 percent of the alpha-hydroxy carboxylic acid is photochemically converted to the corresponding alcohol. When a semiconductor catalyst material as disclosed herein is present when the alpha-hydroxy carboxylic acid is irradiated, then the photochemical reaction yields from about 17 percent to about 46 percent of the corresponding alcohol, the yield being based on the amount of alpha-hydroxy carboxylic acid reacted.

Other hydrocarbon reaction products from the photochemical decarboxylation of alpha-hydroxy carboxylic acids include acids, diols, aldehydes and lactones. The photochemical decarboxylation of lactic acid in accordance with this invention produces a major hydrocarbon product of ethanol and minor products of propionic acid, acetic acid, acetaldehyde alpha-methyl-gamma-butyrolactone, 2,3-butanediol, methanol, butanol, acetone, alpha-ketoglutaric acid, citric acid, gloxylic acid, fumaric acid and other polyhydroxy and polycarboxylic compounds.

The catalyst in accordance with the present invention comprises a semiconductor material. The catalyst may comprise a p-type or an n-type semiconductor which when irradiated with light energy greater than the semiconductor's band gap (Eg) causes formation of electron-hole pairs. These unfilled orbitals may act as sites for redox reactions between the semiconductor and a substance in contact with the semiconductor such as the alpha-hydroxy carboxylic acid. The holes in an n-type semiconductor material, at energies characteristic of the valence band, are effectively strong oxidizing agents and can extract electrons. The electrons of an n-type semiconductor material, at energies characteristic of the valence band, are effectively strong reducing agents and can donate electrons. A discussion of semiconductor materials in general can be found in *Optical Processes in Semiconductors*, J. I. Pankove, Dover Publications, Inc., New York, N.Y. (1975).

Semiconductor materials in accordance with this invention include oxides of antimony, cerium, indium, iron, molybdenum, tantalum, tin, titanium, tungsten, vanadium, zinc, zirconium, lanthanum, niobium and manganese; cadmium sulfide; metal titanium oxides; carbonates of calcium, strontium and barium; nitrates of aluminum, chromium, cobalt and lanthanum; and combinations thereof. The semiconductor materials may be doped, such as titanium dioxide doped with aluminum, beryllium, chromium, cadmium, cobalt, platinum, ruthenium dioxide or combinations thereof; zinc oxide doped with silver and/or platinum; and strontium titanate doped with chromium, cobalt, nickel, platinum, ruthenium or combinations thereof. Metal titanium oxides have been found to be highly selective for the photochemical decarboxylation of alpha-hydroxy carboxylic acids to corresponding alcohols.

Because of their high selectivity for forming the corresponding alcohols, metal titanium oxides are preferred catalysts of the subject invention. Generally, any metal may be combined with a titanium oxide to form a metal titanium oxide. Most preferably, the catalyst of the present invention comprises a semiconductor material that includes a metal titanium oxide selected from the group consisting of magnesium titanate, calcium titanate, strontium titanate, barium titanate, bismuth titanate and zinc magnesium titanate.

Semiconductor materials generally may be doped and/or platinized to yield more active materials having enhanced properties. As applied to photochemical reactions wherein the semiconductor has a catalytic effect, doping and/or platinizing may increase the reaction rate and/or yield of the photochemical reaction. When the catalyst of the present invention is an oxide material such as titanium dioxide, a carbonate or a nitrate, or cadmium sulfide or a combination thereof, then doping and/or platinizing enhances the catalyst's ability to photochemically decarboxylate an alpha-hydroxy carboxylic acid to the corresponding alcohol. However, it has been observed that when the catalyst is a metal titanium oxide, then doping and/or platinizing has unexpectedly been found to generally decrease the metal titanium oxide's ability to photochemically decarboxylate an alpha-hydroxy carboxylic acid to an alcohol. Thus, the semiconductor material which comprises the catalyst of the present invention may or may not be doped and/or platinized to yield optimum catalytic performance.

The above-described catalyst may be used in a process of the present invention to yield alcohols from the photochemical decarboxylation of alpha-hydroxy carboxylic acids. In accordance with the process of this invention an alpha-hydroxy carboxylic acid is contacted with a catalyst comprising a semiconductor material and irradiated to cause the photo-induced decarboxylation of the alpha-hydroxy carboxylic acid to its corresponding alcohol.

The alpha-hydroxy-carboxylic acid is disposed in a solution. The solution may be an aqueous solution or a suitable organic solution in which the alpha-hydroxy carboxylic acid is soluble and which solvent does not interfere with the catalyst's activity nor block high spectral energy light such as acetonitrile. Preferably, the alpha-hydroxy carboxylic acid solution is an aqueous solution. The alpha-hydroxy carboxylic acid may be present in solution at any initial molar concentration. For enhanced reactivity it is preferred that the alpha-hydroxy-carboxylic acid be present in solution at an initial molar concentration of from about 0.13M to about 2.64M. Optimally the alpha-hydroxy carboxylic acid is present in solution at an initial molar concentration of about 0.88M.

The catalyst is placed in contact with the alpha-hydroxy carboxylic acid. The catalyst may be in the form of a powder wherein it is preferably mixed uniformly into the alpha-hydroxy carboxylic acid solution or the catalyst powder may be colloidal and suspended in the solution. The semiconductor catalyst material may be present at any concentration. Preferably the semiconductor catalyst material is present in an alpha-hydroxy carboxylic acid solution at a concentration of from about 2.5 mg/ml to about 45 mg/ml. More preferably, the semiconductor catalyst material is present in an alpha-hydroxy carboxylic acid solution at a concentration of from about 7.5 mg/ml to about 15 mg/ml.

The catalyst may also be deposited on a fixed bed or be disposed in a reaction chamber in the form of packed pellets. This process may be adaptable for both batch and continuous operations.

The process may proceed under a wide range of temperatures, pressures and atmospheres and still provide the photo-induced decarboxylation of alpha-hydroxy carboxylic acids to the corresponding alcohols. Optimum reaction conditions will be dependent on the particular reactants used. Preferably the photo-induced decarboxylation of alpha-hydroxy carboxylic acids in the presence of a semiconductor catalyst material occurs at temperatures of from about 0° C. to about 100° C., pressures of from about 1 atmosphere to about 10 atmospheres and under an oxidative or inert atmosphere. More preferred, the photochemical reaction occurs at from about 0° C. to about 50° C., from about 1 to about 3 atmospheres, and under an atmosphere of nitrogen, helium, argon, oxygen or air. Optimally, alpha-hydroxy carboxylic acids are photochemically converted to the corresponding alcohols in the presence of semiconductor catalyst materials at temperatures of from about 20° C. to about 30° C., at about atmospheric pressure and under an atmosphere of nitrogen, argon or air.

In accordance with the process of this invention, the alpha-hydroxy carboxylic acid solution in contact with a catalyst, hereinafter referred to as the catalyzed solution, is irradiated to induce a photochemical reaction. The source of irradiation may be solar or an artificial light. The light source preferably includes wavelengths in the range of from about 2,200Å to about 14,000Å. Optimally, the light source irradiating the catalyzed solution include light having a substantial irradiation spectrum in the range of from about 2,200Å to about 4,000Å.

The catalyzed solution is preferably exposed to irradiation for a period of from about two hours to about 65 hours. More preferably the catalyzed solution is exposed to a light source for from about 8 hours to about 24 hours.

The photo-induced decarboxylation of alpha-hydroxy carboxylic acids in accordance with the present invention yields primarily the corresponding alcohol and secondarily other alcohols, acids, diols, aldehydes and lactones. The hydrocarbon products may be separated from the catalyzed solution and from each other by known separation techniques such as distillation and/or extraction. The catalyst, if suspended in the catalyzed solution may be recovered by well-known filtration, precipitation or centrifugal techniques.

The alcohols produced by this process are useful as fuels and as intermediates for the production of other chemicals.

EXAMPLES

The following examples more thoroughly illustrate the present invention and are not intended in any way to be limitative thereof.

Each example involved irradiating an alpha-hydroxy carboxylic acid. For purposes of the examples and analysis of the reaction products lactic acid was the alpha-hydroxy carboxylic acid. It is understood that any alpha-hydroxy carboxylic acid would react in a manner similar to that exhibited by lactic acid hereunder. For the same purposes, the semiconductor catalysts utilized were titanium dioxide and metal titanium oxides. It is understood that any semiconductor material would generally perform in a manner similar to that exhibited by titanium dioxide and metal titanium oxides.

The examples were performed in a 500 ml photochemical reaction vessel containing a magnetic stirring bar therein and a water-cooled double-walled quartz immersion well which maintained the reaction at a temperature of between about 23° C. and about 28° C. A water-cooled Friedrich condenser was disposed over the reaction vessel to minimize loss of hydrocarbon products, such as ethanol, by evaporation. The reaction vessel was closed to the atmosphere above the condenser. A lactic acid solution was prepared by dissolving 31.5 gms 88 percent lactic acid (0.88M) into 350 ml of distilled water. A known amount of catalyst in the form of a powder was then admixed into the lactic acid solution to form a catalyzed solution. In the control example, Example 1, no catalyst was added.

The catalyzed solution was then disposed in the photochemical reaction vessel and stirred while irradiated with a light source having the following spectral energy distribution (recorded in watts):

| Far UV | 2,200–2,800Å | 29.2 watts |
|---|---|---|
| Middle UV | 2,800–3,200Å | 32.8 watts |
| Near UV | 3,200–4,000Å | 32.9 watts |
| Visible | 4,000–10,000Å | 87.2 watts |
| infrared | 10,000–14,000Å | 20.6 watts |

Each solution was irradiated for a period of time of from about two hours to about 32 hours. The reacted solution was analyzed by gas chromatography and gas chromatography/mass spectroscopy to identify the photoproducts. Alcohols and acids were identified by gas chromatography by comparing their retention times with the retention times of standardized samples. The concentrations of various photoproducts were determined by using a ratio of the measurement of gas chromatograph area of the product to the gas chromatograph area of a standard. A detector response factor, RF, was determined to account for the difference in molar response for each product. Product concentrations were determined as follows:

$$\left[ \begin{array}{c} \text{Product} \\ \text{Concentration} \end{array} \right] = RF \times \left[ \begin{array}{c} \text{Standard} \\ \text{Concentration} \end{array} \right] \times \frac{\text{Product G.C. area}}{\text{Standard G.C. area}}$$

EXAMPLES 1–16

These Examples demonstrate the effectiveness of the catalysts of this invention.

In Examples 1–16, the aforedescribed experimental procedure was performed with solutions containing no catalyst, Example 1; various concentrations of titanium dioxide catalyst, Examples 2–6; and various concentrations of various metal titanium oxides, Examples 7–16. Each example was carried out at atmospheric pressure. Each example was irradiated for a period of time based on sampling until the formation of photo-products ceased, at which time the reaction products were characterized. Ethanol and 2,3-butanediol were measured as photoproducts.

As can be seen from Table 1, which reports the final percent ethanol and 2,3-butanediol yields, as a percent based on the number of moles of alpha-hydroxy carboxylic acid reacted, the titanium dioxide catalyzed solutions yielded about 30 percent more ethanol than the control which did not utilize a catalyst. The metal titanium oxide catalyzed solutions selectively formed ethanol in yields that exceeded the control reaction by more than 100 percent.

TABLE 1

| ALCOHOL SELECTIVITY UTILIZING CATALYSTS OF THE INVENTION | | | |
|---|---|---|---|
| Example | Catalyst | Percent Ethanol Yield | Percent 2.3 Butanediol Yield |
| 1 | None | 15 | |
| 2 | 2.5 mg/ml Titanium dioxide | 23 | 9 |
| 3 | 5 mg/ml Titanium dioxide | 17 | 7 |
| 4 | 10 mg/ml Titanium dioxide | 23 | 6 |
| 5 | 41 mg/ml Titanium dioxide | 31 | N.M. |
| 6 | 80 mg/ml Titanium dioxide | 22 | N.M. |

TABLE 1-continued

ALCOHOL SELECTIVITY UTILIZING CATALYSTS OF THE INVENTION

| Example | Catalyst | Percent Ethanol Yield | Percent 2.3 Butanediol Yield |
|---|---|---|---|
| 7 | 7 mg/ml Barium titanate | 31 | 3.5 |
| 8 | 14 mg/ml Barium titanate | 31 | 11 |
| 9 | 28 mg/ml Barium titanate | 30 | 7 |
| 10 | 9 mg/ml Calcium titanate | 32 | 11 |
| 11 | 8 mg/ml Magnesium titanate | 36 | 11 |
| 12 | 12 mg/ml Strontium titanate | 28 | N.M. |
| 13 | 5 mg/ml Bismuth titanate | 35 | N.M. |
| 14 | 40 mg/ml Bismuth titanate | 44 | N.M. |
| 15 | 5 mg/ml Zinc Magnesium titanate | 35 | N.M. |
| 16 | 17 mg/ml Zinc Magnesium titanate | 46 | N.M. |

*N.M. the concentration of 2,3-Butanediol was not measured.

EXAMPLES 17–30

These Examples demonstrate the effect of doping and platinizing the catalysts of the present invention.

In these Examples, titanium dioxide and metal titanium oxide powders were doped with hydrogen by heating the catalyst materials under a hydrogen atmosphere in the range of between about 550° C. and about 650° C. for from about 6 to about 8 hours and allowing the powders to cool under a hydrogen atmosphere. The doped catalysts were then mixed into lactic acid solutions as described hereinabove and irradiated by a light source to induce the photochemical decarboxylation of lactic acid.

Titanium dioxide and metal titanium oxides were platinized by mixing 0.5 gm of titanium dioxide or metal titanium oxide in a solution comprising 0.5 g of hexachloroplatinic acid dissolved in 100 ml of 1.2M hydrochloric acid. The titanate-containing platinum solution was purged with argon for 15 minutes and irradiated with a 500W mercury lamp for about 6.2 hours. The solution was purged with nitrogen, then neutralized with sodium hydroxide. Hydroquinone, in an amount of about 0.52 gm in 75 ml of distilled water, was added and the solution was stirred at about 50° C. under a nitrogen atmosphere for about 8 hours. The platinized titanate was filtered, dried and utilized as described hereinabove as semiconductor catalyst materials for the photoinduced decarboxylation of lactic acid.

As in Example 1, each example was irradiated until, based on sampling, the formation of additional photoproducts ceased. The final reaction mixture was characterized and the percent ethanol yields, based on the number of moles of lactic acid reacted are reported in Table 2. As is shown by the percent ethanol reported for Examples 17–31 in Table 2, doping and platinizing enhance the catalytic activity of titanium dioxide and generally decrease the catalytic ability of metal titanium oxides.

TABLE 2

ALCOHOL YIELD AS A FUNCTION OF DOPING OR PLATINIZING THE CATALYST

| Example | Catalyst | Percent Ethanol Yield |
|---|---|---|
| 17 | None | 15 |
| 18 | 5 mg/ml Titanium dioxide | 17 |
| 19 | 5 mg/ml Titanium dioxide, doped | 27 |
| 20 | 5 mg/ml Titanium dioxide, platinized | 22 |
| 21 | 0.5 mg/ml Titanium dioxide, platinized | 22 |
| 22 | 5 mg/ml Bismuth titanate | 35 |
| 23 | 40 mg/ml Bismuth titanate | 44 |
| 24 | 40 mg/ml Bismuth titanate, doped | 44 |
| 25 | 5 mg/ml Bismuth titanate, platinized | 26 |
| 26 | 0.5 mg/ml Bismuth titanate, platinized | 21 |
| 27 | 5 mg/ml Zinc-magnesium titanate | 35 |
| 28 | 17 mg/ml Zinc-magnesium titanate | 46 |
| 29 | 17 mg/ml Zinc-magnesium titanate, doped | 40 |
| 30 | 5 mg/ml Zinc-magnesium titanate, platinized | 42 |
| 31 | 0.5 mg/ml Zinc-magnesium titanate, platinized | 33 |

EXAMPLES 32–43

The effect of varying the range of light wavelengths that irradiate the catalyzed solution is demonstrated in Examples 32–43.

The quartz immersion well, the sidewalls of which the irradiating light must travel through prior to reaching the catalyzed solution, is characterized as having 70 percent transmittance at 2,000Å. This well can also be fitted with Vycor and Pyrex glass sleeves, both trademarks of the Corning Glass Co., Corning, N.Y. The Vycor sleeve has a 50 percent transmittance at 2,400Å. The Pyrex sleeve has a 50 percent transmittance at 3,100Å. Hence, less high energy light reaches the catalyzed solution when the Vycor sleeve is inserted in the quartz well and even less when the sleeve is a Pyrex sleeve. By utilizing the Vycor and Pyrex sleeves in the quartz immersion well, the catalysts' performance could be observed when various high energy light ranges were reduced or effectively blocked from reaching the catalyzed solution.

Table 3 summarizes the effect that blocking high energy light ranges has on catalyst performance. Generally, with reduced energy light, the catalysts' activities are reduced. However, various catalysts perform at different efficiencies. The metal titanium oxides remain efficient catalysts when a Vycor or Pyrex sleeve is present in the quartz immersion well between the light source and the catalyzed solution. Titanium dioxide remains efficient when a Vycor sleeve is interposed between the light source in the quartz immersion well and the catalyzed solution, but is not effective when the sleeve is a Pyrex sleeve. An uncatalyzed lactic acid solution shows no significant photochemical activity when either a Vycor or a Pyrex sleeve is interposed in the quartz immersion well between the solution and the light source. Thus, the catalyzed solutions of this invention are more photochemically active in the absence of high energy light than non-catalyzed alpha-hydroxy carboxylic acid solutions, and the metal titanium oxide catalyzed solutions remain substantially photochemically active in the absence of high energy light.

TABLE 3

ALCOHOL YIELD AS A FUNCTION OF LIGHT WAVELENGTH AND CATALYST

| Example | Catalyst | Filter | Percent Ethanol Yield |
|---|---|---|---|
| 32 | None | quartz | 15 |
| 33 | None | quartz and Vycor | 4 |
| 34 | None | quartz and Pyrex | 4 |
| 35 | 5 mg/ml Titanium dioxide | quartz | 17 |
| 36 | 5 mg/ml Titanium dioxide | quartz and Vycor | 14 |
| 37 | 5 mg/ml Titanium dioxide | quartz and Pyrex | 2 |
| 38 | 40 mg/ml Bismuth titanate | quartz | 44 |
| 39 | 40 mg/ml Bismuth titanate | quartz and Vycor | 34 |
| 40 | 40 mg/ml Bismuth titanate | quartz and Pyrex | 13 |
| 41 | 17 mg/ml Zinc-magnesium titanate | quartz and Vycor | 46 |
| 42 | 17 mg/ml Zinc-magnesium titanate | quartz and Vycor | 45 |
| 43 | 17 mg/ml Zinc-magnesium titanate | quartz and Pyrex | 19 |

The selection of the semiconductor catalyst materials, alpha-hydroxy carboxylic acids, products derived from the photo-induced decarboxylation thereof and reactant conditions can be determined from the preceeding specification disclosure provided without departing from the spirit of the invention herein disclosed and described; the scope of the invention including modifications and variations that fall within the scope of the appended claims.

We claim:

1. A process for the photochemical decarboxylation of an alpha-hydroxy carboxylic acid to the corresponding alcohol which process comprises irradiating a mixture of (a) a solution of an alpha-hydroxy carboxylic acid and (b) a metal titanate.

2. The process in accordance with claim 1 wherein said alpha-hydroxy carboxylic acid is selected from the group consisting of mandelic acid, alpha-hydroxy isobutyric acid, alpha-ethyl-alpha-hydroxy butyric acid, alpha-hydroxy-alpha-methyl butyric acid, alpha-isopropyl-mandelic acid, lactic acid, benzylic acid, phenolactic acid and mixtures thereof.

3. The process in accordance with claim 1 wherein said alpha-hydroxy carboxylic acid is lactic acid.

4. The process in accordance with claim 1 wherein said metal titanate is selected from the group consisting of magnesium titanate, calcium titanate, strontium titanate, barium titanate, bismuth titanate and zinc magnesium titanate.

5. The process in accordance with claim 1 wherein said alpha-hydroxy carboxylic acid solution is an aqueous solution.

6. The process in accordance with claim 1 wherein said alpha-hydroxy carboxylic acid is initially present in solution at a molar concentration of from about 0.13M to about 2.64M.

7. The process in accordance with claim 1 wherein said alpha-hydroxy carboxylic acid is initially present in solution at a molar concentration of about 0.88M.

8. The process in accordance with claim 1 wherein said metal titanate is present in said solution at a concentration of from about 2.5 mg/ml to about 45 mg/ml.

9. The process in accordance with claim 1 wherein said metal titanate is present in said catalyzed solution at a concentration of from about 7.5 mg/ml to about 15 mg/ml.

10. The process in accordance with claim 1 wherein said mixture is irradiated for from about two hours to about 65 hours.

11. The process in accordance with claim 1 wherein said mixture is irradiated for about from about 8 hours to about 24 hours.

12. The process in accordance with claim 1 wherein said mixture is irradiated with a light source including light having wavelengths from about 2,200Å to about 14,000Å.

13. The process in accordance with claim 1 wherein said mixture is irradiated with a light source including light having wavelengths from about 2,200Å to about 4,000Å.

* * * * *